US011208679B2

(12) United States Patent
McDaniel et al.

(10) Patent No.: US 11,208,679 B2
(45) Date of Patent: Dec. 28, 2021

(54) METHOD FOR VALIDATING ASSAYS OF BIOLOGICAL SAMPLES

(71) Applicant: THE TRANSLATIONAL GENOMICS RESEARCH INSTITUTE, Phoenix, AZ (US)

(72) Inventors: Timothy K. McDaniel, Phoenix, AZ (US); Muhammed Murtaza, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 245 days.

(21) Appl. No.: 16/099,664

(22) PCT Filed: May 31, 2017

(86) PCT No.: PCT/US2017/035330
§ 371 (c)(1),
(2) Date: Nov. 7, 2018

(87) PCT Pub. No.: WO2017/210372
PCT Pub. Date: Dec. 7, 2017

(65) Prior Publication Data
US 2019/0153509 A1    May 23, 2019

Related U.S. Application Data

(60) Provisional application No. 62/343,802, filed on May 31, 2016.

(51) Int. Cl.
| C12Q 1/6806 | (2018.01) |
| C12Q 1/6886 | (2018.01) |
| G16B 25/00 | (2019.01) |
| G16B 25/20 | (2019.01) |
| G16B 30/00 | (2019.01) |

(52) U.S. Cl.
CPC ......... *C12Q 1/6806* (2013.01); *C12Q 1/6886* (2013.01); *G16B 25/00* (2019.02); *G16B 25/20* (2019.02); *G16B 30/00* (2019.02); *C12Q 2600/166* (2013.01)

(58) Field of Classification Search
CPC ............... C12Q 1/6806; C12Q 1/6886; C12Q 2600/166; G16B 25/00; G16B 30/00; C12C 2600/166
See application file for complete search history.

(56) References Cited

U.S. PATENT DOCUMENTS

| 2007/0092869 A1 | 4/2007 | Fulmer-Smentek et al. |
| 2015/0292001 A1 | 10/2015 | Willey et al. |
| 2015/0366835 A1* | 12/2015 | Pogue-Geile ........ C12Q 1/6886 |
| | | 514/492 |

FOREIGN PATENT DOCUMENTS

| WO | 2014/127484 A1 | 8/2014 |
| WO | 2017/205540 A1 | 11/2017 |

OTHER PUBLICATIONS

Fardin et al., "Normalization of low-density microarray using external spike-in collrols: analysis of macrophage cell lines expression profile", BMC Genomics, 8:1-19 (Jan. 17, 2007).
Tembe et al., "Open-access synthetic spike-in mRNA-seq data for cancer gene fusions", BMC Genomics, 15:1-9 (Sep. 30, 2014).
Zook et al., "Synthetic spike-in standards improve run-specific systematic error analysis for DNA and RNA sequencing", PLoS One, 7:1-10 (Jul. 31, 2012).
Mandel, P., et al. Les acides nucleiques du plasma sanguine chez l'homme. C R Seances Soc Biol Fil 1948; 142 (3-4):241-243.
Schwarzenbach, H., et al. Cell-free nucleic acids as biomarkers in cancer patients. Nature Reviews Cancer 2011; 11(67):426-437.
Alix-Panabieres, C., et al. Circulating tumor cells and circulating tumor DNA. Annual Review of Medicine 2012;63:199-215.
Roth, C., et al. Apoptosis-related deregulation of proteolytic activities and high serum levels of circulating nucelosomes and DNA in blood correlate with breast cancer progression. BMC Cancer 2011; 11:4.
Fleischhacker, M., et al. Circulating nucleic acids (CNAs) and cancer—a survey. Biochimica et biophysica acta 2007; 1775(1):181-232.
Bendich, A., et al. Circulating DNA as a Possible Factor in Oncogenesis. Science 1965; 148(3668):374-376.
Laktaniov, P., et al. Cell Surface Bound Nucleic Acids: Free and Cell Surface Bound Nucleic Acids in Blood of Healthy Donors and Breast Cancer Patients. Annals of the New York Academy of Sciences 2004; 9(1022):221-227.
Schwarzenbach, H., et al. Cell-free tumor DNA in blood plasma as a marker of ciiculating tumor cells in prostate cancer. Clinical Cancer Research 2009; 15(3):1032-1038.
Punnoose, E. A., et al. Evaluation of Circulating Tumor Cells and Circulating Tumor DNA in Non-Small Cell Lung Cancer: Association with Clinical Endpoints in a Phase II Clinical Trial of Pertuzumab and Erlotinib. Clinical Cancer Research 2012; 18(8):2391-2401.
Pao, W., et al. Epidermal growth factor receptor mutation testing in lung cancer: searching for the ideal method. Clinical Cancer Research 2007; 13(17):4954-4955.
Baselga, J., et al. Relationship between tumor biomarkers and efficacy in EMILIA, a phase III study of trastuzumab emtansine in HER2-positive metastatic breast cancer. Clin Cancer Res 2016; 22(15):3755-3763.
Kuhn, Kenneth et al., "A novel, high-performance random array platform for quantitative gene expression profiling", Genome Research, 14(11):2347-2356 (Nov. 1, 2004).
Bugovsky, Stefan et al., "Quality control of oligonucleotide synthesis by means of matrix-assisted laser desorption/ionization linear time-of-flight mass spectrometry on a nanocoated disposable target", Rapid Communications in Mass Spectrometry, 30(5):665-668 (Mar. 15, 2016).

\* cited by examiner

*Primary Examiner* — Cynthia B Wilder
(74) *Attorney, Agent, or Firm* — Casimir Jones, S.C.; J. Mitchell Jones

(57) ABSTRACT

The invention provides a method for validating patient-specific oligos using spike-in sequences.

20 Claims, 1 Drawing Sheet

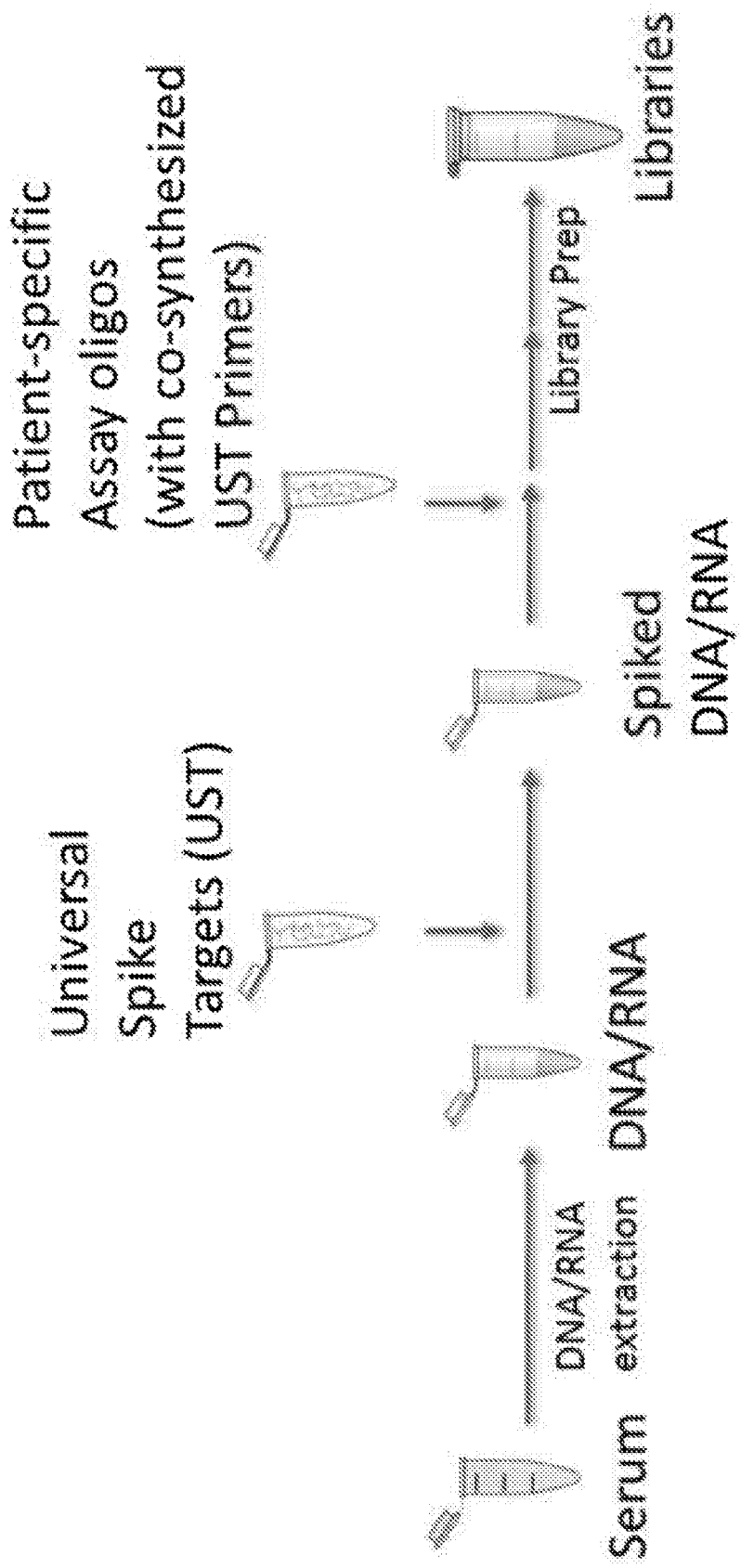

METHOD FOR VALIDATING ASSAYS OF BIOLOGICAL SAMPLES

RELATED APPLICATION DATA

This application is the U.S. National Stage of International Application No. PCT/US2017/035330, filed on May 31, 2017, which claims priority to and the benefit of U.S. Provisional Application No. 62/343,802, filed on May 31, 2016, the contents of each of which are hereby incorporated by reference in their entirety entireties.

FIELD OF THE INVENTION

The present invention is related to methods of validating oligonucleotides ("oligos") during biological sample analysis using spike-in control oligos.

BACKGROUND OF THE INVENTION

The development of genomic sequencing analysis has facilitated the arrival of personalized medicine. In such testing, two general approaches are generally applied. Comprehensive tests, such as whole-genome sequencing or whole-exome sequencing, are expensive but offer breadth, such that it is not necessary to know prior to testing what variants might be present in a biological sample. Targeted tests, such as single-gene or multi-gene panels, are less expensive, but require some assumptions about what variants might be present in the sample; any useful variants that are present in the patient sample but not addressed by the test design will be missed. A strategy that optimizes this cost/comprehensiveness trade-off could be achieved in cases where one anticipates to test the same portions of the genome in the same patient repeatedly over time. In such cases, one could initially use comprehensive testing to identify patient-specific mutations and then perform less expensive targeted testing on subsequent samples using an assay designed to test only the regions of the genome containing one or more patient-specific mutations identified by the first test. However, factors that limit the clinical application of patient-specific genome analysis are the cost and complexity of validating the analytic performance of the patient-specific oligos used in these methods. Whereas the development of genome screening technologies has reduced the cost of comprehensive analysis, the practical limitations of validating the patient-specific oligos still exist. Accordingly, the current genetic application of personalized medicine has been limited to expensive broad testing or performing targeted testing using the same set of loci from patient to patient. However, in order to truly take advantage of the information conveyed in a patient's genome, the commercial and practical limitations in using multiple patient-specific oligos must be overcome.

For example, the field of liquid biopsy in cancer requires a sensitive and accurate system for detecting circulating tumor DNA (ctDNA). Given the concentration of ctDNA compared to that of the patient's normal DNA is very low, ctDNA screening would be more useful if multiple targets of ctDNA are evaluated as a means of achieving greater sensitivity. If ctDNA were used as a way of monitoring cancer treatment effectiveness or disease recurrence, screening multiple targets of ctDNA becomes cost prohibitive. Based on the current technology in the art, this requires sequencing at every time point a large enough sampling of the genome to ensure capturing multiple somatic mutations. If patient-specific oligos that target the patient's specific set of ctDNA markers could be used, then monitoring disease progression or treatment efficacy with ctDNA would only require the whole genome or exome be sequenced once to determine the patient-specific somatic mutations in ctDNA. The use of patient-specific oligos would also reduce the sequencing footprint to reduce the cost of subsequent sample analysis. Current procedures for validating assays are not practical for validating patient-specific oligos, as they require each test be run a large number of times to establish the assay's analytic performance characteristics. Such testing greatly increases the cost of using patient-specific oligos and introduces a significant time delay in being able to use the patient-specific tests. Therefore, there is a need for a cost-effective and practical way of validating patient-specific oligos.

SUMMARY OF THE INVENTION

The invention is a design for sets of controls and methods for their use for in-line validation of assays of biological samples that use patient-specific oligos. The method typically comprises extracting DNA or RNA from a patient sample to produce a DNA or RNA sample; introducing a plurality of sets of spike-in oligo sequences into the DNA or RNA sample to produce a spiked sample, wherein the plurality of sets of spike-in sequences consists of known sequences at known concentrations; cosynthesizing synthesis-control oligos and patient-specific oligos; and assaying the spiked sample with the control oligos and the patient-specific oligos. Reading out the counts of spike-in sequences determines the dose-response characteristics of the synthesis-control oligos, which act as proxies for those of the of the patient-specific oligo in the assay, and thus provide a quality control check for the batch synthesis of the patient-specific oligos.

In some aspects, the present invention is directed to a method of validating a patient-specific oligo, the method comprising: extracting DNA or RNA from a patient sample to produce a DNA or RNA sample; introducing a plurality of sets of spike-in sequences into the DNA or RNA sample to produce a spiked sample, wherein the plurality of sets of spike-in sequences comprises spike-in sequences of known concentrations; cosynthesizing synthesis-control oligos and the patient-specific oligo; and assaying the spiked sample with the synthesis-control oligos to produce a read out of the counts of the set of spike-in sequences; and comparing the counts from the set of spike-in sequences with the known concentrations of the spike-in sequences, wherein the limit of detection (LOD) and the dynamic range for the patient-specific oligo are validated when the counts from the set of spike-in sequences correspond to the known concentrations of the spike-in sequences.

In other aspects, the present invention relates to a method of validating a patient-specific oligo, the method comprising: extracting DNA or RNA from a patient sample to produce a DNA or RNA sample; introducing a plurality of sets of spike-in sequences into the DNA or RNA sample to produce a spiked sample, wherein the plurality of sets of spike-in sequences comprises spike-in sequences of known concentrations; assaying the spiked sample with synthesis-control oligos to produce a read out of the counts of the set of spike-in sequences, wherein the synthesis-control oligos are cosynthesized with the patient-specific oligo; and comparing the counts from the set of spike-in sequences with the known concentrations of the spike-in sequences, wherein the LOD and the dynamic range for the patient-specific oligo are validated when the counts from the set of spike-in sequences correspond to the known concentrations of the spike-in sequences.

In some aspects, assaying the spiked sample with synthesis-control oligos comprises performing polymerase chain reaction (PCR) or sequencing with the synthesis-control oligos.

In other aspects, the PCR is digital PCR or quantitative PCR.

In some embodiments, the plurality of set of spike sequences is introduced to the DNA or RNA sample prior to library synthesis.

In other embodiments, the counts of spike-in sequences acts as a proxy for the dose-response characteristics of the patient-specific oligo in the assaying step.

In one embodiment, the plurality of sets of spike-in sequences comprises at least 4 sets of spike-in sequences.

In one aspect, a set of spike-in sequences comprises: a unique reference sequence; and a plurality of near-neighbor sequences, wherein each near-neighbor sequence comprises at least one substitution, insertion, and/or deletion compared to the reference sequence.

In another aspect, the concentration of each near-neighbor sequence is less than the concentration of the reference sequence.

In certain embodiments, the ratios of the concentration of each near-neighbor sequence to the concentration of the reference sequence spans at least four orders of magnitude.

In other embodiments, the ratios of the concentration of the plurality of near-neighbor sequences to the concentration of the reference sequence comprise 1:10, 1:100, 1:1000, and 1:10,000.

In some aspects, each set of spike-in sequences comprises the same number of near-neighbor sequences.

In other aspects, the plurality of sets of spike-in sequences comprises the same set of ratios of the concentration of each near-neighbor sequence to the concentration of the reference sequence.

In one embodiment, the counts from the set of spike-in sequences corresponds to the known concentrations of the spike-in sequences when ratios of the near-neighbor sequences in relation to the reference sequence based on the counts is within 20%, 15%, 10%, 5%, or 1% of ratios of the near-neighbor sequences in relation to the reference sequence based on the known concentrations.

In another embodiment, the LOD and the dynamic range for the patient-specific oligo is validated when the ratios based on the counts is within 1% of the ratios based on the known concentrations.

In some aspects, the patient sample is a liquid sample containing cell-free DNA (cfDNA) and/or cell-free RNA (cfRNA). In other aspects, the cfDNA and/or cfRNA indicate a mutation and/or change in expression in a gene selected from the group consisting of PD-L1, ERCCI, EGFR, TS, AREG, EREG, VEGFR2, EML4ALK, ROSI, RET, c-Met, FGFRI, KRAS, BRAF, NRAS, Her-2, PIK3CA, KIT, GNAQ, and GNA11.

In yet other aspects, the patient-specific oligo detects circulating tumor DNA (ctDNA).

In certain embodiments, the patient has or is suspected of having cancer. In one aspect, the cancer is selected from the group consisting of head and neck, periampullary, colorectal, lung, melanoma, gastric, esophageal, breast, ovarian, sarcoma, renal cell, prostate, gastrointestinal stromal tumor (GIST) and pancreatic cancer.

In certain implementations, the plurality of set of spike sequences is introduced added to the DNA or RNA sample prior to library synthesis. In some embodiments, the plurality of sets of spike-in sequences comprises at least 10 sets of spike-in sequences.

One set of spike-in sequences comprises a reference sequence and a plurality of near-neighbor sequences. A near-neighbor sequence comprises at least one substitution compared to the reference. In some embodiments, the concentration of each near-neighbor sequence in a set of spike-in sequences is less than the concentration of the reference sequence. In certain aspects, the ratios of the concentration of each near-neighbor sequence to the concentration of the reference sequence spans at least four orders of magnitude. For example, the ratios of the concentration of each near-neighbor sequence to the concentration of the reference sequence comprise 1:10, 1:100, 1:1000, and 1:10,000.

In selected implementations, each set of spike-in sequences comprises the same number of near-neighbor sequences. In some aspects, the plurality of sets of spike-in sequences comprises the same set of ratios of the concentration of each near-neighbor sequence to the concentration of the reference sequence.

In one embodiment, the patient sample is a liquid sample containing cell-free DNA. In a preferred embodiment, the patient-specific oligo detects circulating tumor DNA (ctDNA).

Additional objectives, advantages and novel features will be set forth in the description which follows or will become apparent to those skilled in the art upon examination of the drawings and detailed description which follows.

BRIEF DESCRIPTION OF THE DRAWINGS

FIG. 1 depicts an embodiment of how the universal spike target (UST) could be used in the validation of the synthesis a sequencing library.

The headings used in the FIGURES should not be interpreted to limit the scope of the claims.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps. Unless specifically noted, it is intended that the words and phrases in the specification and the claims be given their plain, ordinary, and accustomed meaning to those of ordinary skill in the applicable arts.

As used herein, the term "patient" refers to the donor of a sample. The patient may be any animal, for example, mammals or birds. In preferred embodiments, the patient is a human.

As used herein, the term "oligo" refers to single-stranded or double-stranded nucleic acid sequences. In preferred embodiments, an oligo may be a primer for sequence analysis or applications involving nucleic acid amplification. These oligos may use both DNA and RNA as the analyte.

As used herein, the term "synthesis-control oligo" refers to an oligo that is complementary to and binds with all of the spike-in sequences in a set, which includes the reference sequence and all of the near-neighbor sequences.

As used herein, the term "spike target" refers to the spike-in sequences of the invention. Spike targets are single or double stranded oligos with a collective spread of lengths corresponding to the spread in a sample, for example, a typical sample for ctDNA analysis.

As used herein, the term "spike-in sequence" refers to an oligo with a sequence that is unrelated to any sequence in the sample from the patient and that serves as a template for a synthesis-control oligo.

As used herein, the term "co-synthesized" refers to oligos that are synthesized by the same method, at the same time, and/or in the same batch.

As used herein, the term "sample" may be any biological sample from a patient. The sample may be a biopsy, for example of a lesion or more specifically a tumor. The sample may also be cell-free DNA from urine, saliva, cerebral spinal fluid, interstitial fluid, or tear. The sample may also be blood or plasma sample.

Cell-free circulating tumor DNA (ctDNA) in the plasma, serum, urine or stool can be used as a liquid biopsy. Changes in ctDNA levels have been associated with tumor burden and malignant progression.

The presence of circulating free DNA (cfDNA) in human blood from subjects was first described in 1948 (P. Mandel and P. Métais, Les acides nucléiques du plasma sanguin chez l'homme, Comptes Rendus de l'Académie des Sciences, vol. 142, pp. 241-243, 1948). It was not until 1994 that ctDNA was discovered in the blood of tumor patients (mutated Ras gene fragments) and associated with malignant tumor progression. Approximately 3.3% ctDNA will be released per day from a tumor weighing 100 g (approximately 3×1010 tumor cells) (H. Schwarzenbach, D. S. B. Hoon, and K. Pantel, Cell-free nucleic acids as biomarkers in cancer patients, Nature reviews. Cancer, vol. 11, pp. 426-37, June 2011). Circulating free (tumor) nucleic acids are usually present in the plasma or serum in the form of short fragments of between 70 and 200 bp in length. Very large fragments of up to 21 kb in length have also been detected. The concentration of cfDNA in biological fluids is usually very low and varies greatly between individuals within a range of 1-100 ng/ml. A correlation has nevertheless been confirmed between high cfDNA concentrations (possibly increased by ctDNA) in tumor patients and low concentrations in subjects (C. Alix-Panabières, H. Schwarzenbach, and K. Pantel, Circulating tumor cells and circulating tumor DNA, Annual review of medicine, vol. 63, pp. 199-215, January 2012).

In early tumor development, ctDNA is shed passively by the primary tumor into the bloodstream via apoptotic and/or necrotic processes. Necrotic or apoptotic cells are normally phagocytized by macrophages. Macrophages that digest necrotic cells may release this DNA into surrounding tissue. In vitro cell culture experiments have shown that macrophages are either activated during this process or die off during DNA release (C. Roth, K. Pantel, V. Müller, B. Rack, S. Kasimir-Bauer, W. Janni, and H. Schwarzenbach, Apoptosis-related deregulation of proteolytic activities and high serum levels of circulating nucleosomes and DNA in blood correlate with breast cancer progression, BMC cancer, vol. 11, p. 4, January 2011). The active release of tumor cells may itself be an additional mechanism for the release of ctDNA. Besides, the mechanisms for ctDNA formation described above, Fleischhacker and Schmidt (2007) published that ctDNA can also be released as a consequence of inflammatory processes during tumor progression in tumor patients (M. Fleischhacker and B. Schmidt, Circulating nucleic acids (CNAs) and cancer—a survey, Biochimica et biophysica acta, vol. 1775, pp. 181-232, January 2007). In addition, ctDNA levels are also determined by the rate of degradation by DNases and by physiological filtering of the blood. Nucleic acids in the blood are filtered by the liver and kidneys and have a half-life ranging between 15 minutes and several hours in circulating blood. Bendich et al. (1965) published that double-strand ctDNA was detected for longer in circulating blood than single-strand ctDNA (A. Bendich, T. Wilczok, and E. Borenfreund, DNA as a Possible Factor in Oncogenesis, Science, vol. 148, no. 3668, pp. 374-376, 1965). An excess of dying cells, as often observed in tumors, leads to saturation of the process and to an increased concentration of ctDNA in the blood. In the peripheral blood, this ctDNA circulates primarily in the form of mono- or oligonucleosomes (this first chromatin packaging step of higher cells is a complex of DNA and histones) or is bound to DNA-binding proteins on the surface of blood cells (P. Laktaniov and S. Tamkovich, Cell Surface Bound Nucleic Acids: Free and Cell Surface Bound Nucleic Acids in Blood of Healthy Donors and Breast Cancer Patients, Annals of the New York Academy of Sciences, vol. 9, no. 1022, pp. 221-227, 2004). This ctDNA can be isolated from the blood and used for measuring genetic and/or epigenetic parameters.

ctDNA analysis provides a means of demonstrating tumor progression at a molecular level and of documenting the mutational status of the tumor. The detection of mutations in tumor tissue has an influence on disease prognosis and choice of treatment. It is necessary both to know the mutational status of the tumor at diagnosis and to detect newly acquired mutations during the course of treatment. In this connection, it has been possible, using quantitative methods of measurement, to establish a correlation between ctDNA levels and tumor size and stage and/or a poor prognosis (H. Schwarzenbach, C. Alix-Panabières, I. Müller, N. Letang, J. -P. Vendrell, X. Rebillard, and K. Pantel, Cell-free tumor DNA in blood plasma as a marker for circulating tumor cells in prostate cancer, Clinical cancer research: an official journal of the American Association for Cancer Research, vol. 15, pp. 1032-8, February 2009) presenting an opportunity for monitoring patients longitudinally during treatment and for predicting (non-)response to a medication. There is also a strong correlation between the ctDNA mutation data and the mutational status of the primary tumor (E. A. Punnoose, S. Atwal, W. Liu, R. Raja, B. M. Fine, B. G. M. Hughes, R. J. Hicks, G. M. Hampton, L. C. Amler, A. Pirzkall, and M. R. Lackner, Evaluation of Circulating Tumor Cells and Circulating Tumor DNA in Non-Small Cell Lung Cancer: Association with Clinical Endpoints in a Phase II Clinical Trial of Pertuzumab and Erlotinib, Clinical cancer research: an official journal of the American Association for Cancer Research, vol. 18, April 2012). At the present time, mutational status testing is still often performed using formalin-fixed paraffin-embedded material.

A major problem when it comes to detecting the mutational status of a tumor is the lack of specificity and sensitivity of the detection methods. Generally, a relatively large quantity of ctDNA must be present in blood for the performance of ctDNA mutation analyses. Moreover, ctDNA is typically to be found in the presence of a high background of wild-type, circulating DNA, which makes analysis difficult.

In order to detect mutated DNA by means of Sanger sequencing in a wild-type (WT) background, the mutated DNA must account for at least 25% of the total DNA content (W. Pao and M. Ladanyi, Epidermal growth factor receptor mutation testing in lung cancer: searching for the ideal method, Clinical cancer research: an official journal of the American Association for Cancer Research, vol. 13, pp. 4954-5, September 2007). In clinical samples, the proportion of mutated DNA is between 100 and 10,000 times smaller than this which means that mutation detection is impossible using conventional methods. Analytical methods are available for quantifying the concentration of wild-type and mutated DNA simultaneously.

It was observed that some tumor patients develop resistance during drug treatment because of mutations, with individual SNPs (single nucleotide polymorphisms) often being the cause of resistance to a particular therapy. In certain aspects, the methods of the present invention are used to detect SNPs in DNA or RNA from a patient sample. Identification of these SNPs may guide therapeutic treatment of the patient.

In some embodiments, the patient has or is suspected of having head and neck, periampullary, colorectal cancer, lung cancer (e.g., non-small cell lung cancer), melanoma, gastric, esophageal, breast, ovarian, sarcoma, renal cell, prostate, gastrointestinal stromal tumor (GIST) and pancreatic cancers.

In certain aspects, the methods disclosed herein can be used to validate the analysis of gene expression in a patient. Gene expression can be useful for monitoring the course of chemotherapy. While DNA is largely a static molecule in terms of alterations (that is, new mutations in DNA can take a long time to appear), changes in gene expression can occur rapidly, in a matter of days or even hours, and thus may provide a rapid and sensitive means of assessing changes in the tumor, such as those brought about by the effects of drugs. A continuum of values for relative expression (increasing, decreasing or static levels) of the fraction of rare or aberrant transcripts with respect to normal or wild type transcripts can be measured over time in a liquid biopsy (e.g., plasma) from the patient. Upward or downward trends of expression can be linked to patient outcome to specific chemotherapy regimens.

Chemotherapy regimens can differ by cancer type, stage, and patient genetics. Chemotherapy can be tailored to a specific tumor phenotype. Methods of the present invention can be used to monitor response to a specific chemotherapy regimen prior to, throughout, and following treatment. Example chemotherapy regimens include, but are not limited to, treatment of PD-L1 positive cancer with nivolumab; and treatment of colorectal cancer (CRC) with Regorafenib/Cetuximab; crizotinib; FOLFOX; FOLFORI/Bevacizumab; and Regorafinib/Cetuximab.

In another embodiment, the invention provides for quantitatively evaluating expression of drug response determinant genes which can predict the effectiveness of drugs and thus can be used for making treatment decisions. For example, a recent study showed that advanced HER2-positive breast tumors expressed variable amounts of HER-2 and patients with the highest level of expression derived a dramatically better survival benefit from a HERCEPTIN® than those with lower expressions (Baselga J, et al. Relationship between tumor biomarkers and efficacy in EMILIA, a phase III study of trastuzumab emtansine (T-DM1) in HER2-positive metastatic breast cancer. AACR 2013; Abstract LB-63). Moreover, activating mutations in PIK3CA, which blunt the effects of anti-HER-2 drugs such as lapatanib, had no effect on therapy with HERCEPTIN®. If tissue expression levels of HER-2 of these breast cancer patients are reflected in their cell-free RNA (cfRNA), a blood draw rather than a tissue biopsy can be used to get information on expression of HER-2 as well as mutational status of PIK3. For some cancer-associated biomarkers and/or genes (e.g., Her-2) the copy number may vary. This variation could be detected with cfRNA. Analysis of cfRNA with the methods described herein allows for the detection and/or quantitation of gene fusions that are targeted by chemotherapeutic agents. Non-limiting examples of these gene fusions are EML4-ALK, ROS1, and RET.

Measurement of expression of each variant or emerging resistance mutation in these genes from the plasma of patients undergoing therapy can be critical for optimal patient care. Specific drugs that are active in only certain fusions or mutations in these genes can be deployed to help the patient if rapid and accurate diagnosis of these gene fusions occur. Obtaining tissue biopsies of patients undergoing therapy is not practical for these patients. The methods described herein allow for the validation of liquid biopsies which can be analyzed over time to determine the presence and expression levels of each variant or emerging resistance mutation in these genes.

Non-limiting example of genes associated with response to chemotherapy that can be measured according to the methodology described herein include: EGFR, KRAS, BRAF, NRAS, JAK2, ALK, PDGFRA, IDH1, IDH2, and KIT. In some aspects of the invention, the biomarker is a mutation in a gene or fusion transcript selected from the group consisting of PD-L1, ERCC1, EGFR, TS, AREG, EREG, VEGFR2, EML4ALK, ROS1, RET, c-Met, FGFR1, KRAS, BRAF, NRAS, Her-2, PIK3CA, KIT, GNAQ, and GNA11.

In some embodiments, the gene that is detected and/or quantified for expression in the sample is listed below in Table 1.

TABLE 1

| DNA and/or RNA | Colon | Lung | Melanoma |
|---|---|---|---|
| PD-L1 | PD-L1 | PD-L1 | PD-L1 |
| ERCC1 | ERCC1 | ERCC1 | |
| EGFR | EGFR | EGFR | |
| TS | TS | TS | |
| AREG | AREG | | |
| EREG | EREG | | |
| VEGFR2 | VEGFR2 | | |
| EML4ALK | | EML4ALK | |
| ROS1 | ROS1 | | |
| RET | RET | | |
| c-MET | | c-MET | |
| FGFR1 | | FGFR1 | FGFR1 |

In yet other embodiments, the gene and/or mutation that is detected and/or quantified for expression in the sample is listed below in Table 2.

TABLE 2

| DNA and/or RNA | Colon | Lung | Melanoma |
|---|---|---|---|
| KRAS | | G12C | G12C |
| KRAS | | G12V | G12V |
| KRAS | | G12D | G12D |
| KRAS | | G12A | G12A |
| KRAS | | G12S | G12S |
| KRAS | | G12D | G12D |
| KRAS | | Q61H | |

TABLE 2-continued

| DNA and/or RNA | Colon | Lung | Melanoma |
|---|---|---|---|
| EGFR | | L858R | |
| EGFR | | (Exon 19 Deletions) ΔE746-A750 | |
| EGFR | | L861Q | |
| EGFR | | T790M | |
| EGFR | | G719S | |
| BRAF | V600E | V600E | V600E |
| BRAF | | | V600K |
| NRAS | Q61K | | |
| NRAS | Q61L | | |
| NRAS | Q61R | | |
| HER2 | | (Exon 19 and/or 20 Insertions) HER2 ins | |
| PIK3CA | H1047R | H1047R | |
| PIK3CA | H1047L | H1047L | |
| PIK3CA | E542K | E542K | |
| PIK3CA | E545K | E545K | |
| KIT | | | W577R |
| KIT | | | L576P |
| KIT | | | V559A |
| KIT | | | K642E |
| GNAQ | | | Q209L |
| GNA11 | | | Q209L |

In some embodiments, the invention relates to using a plurality of sets of spike-in sequences (also referred herein as universal spike targets or USTs) in a patient sample to facilitate multiplexed patient-specific applications, for example screening samples using patient-specific oligos. In certain aspects, the spike-in sequences are less than 500 nucleotides in length. In other aspects, the length of the spike-in sequences is between 20 and 500 nucleotides, between 20 and 400 nucleotides, between 20 and 300 nucleotides, between 20 and 200 nucleotides, between 100 and 500 nucleotides, between 100 and 400 nucleotides, between 100 and 300 nucleotides or between 100 and 200 nucleotides. In one embodiment, the length of the spike-in sequences mimics the size of the corresponding DNA and/or RNA to be analyzed in the patient samples. In some implementations, for example for validating cell-free DNA samples, the spike-in sequences are between 100-200 nucleotides in length, such as around 150, 160, 170, 180, or 190 nucleotides in length.

In certain aspects, the invention makes use of at least one set of spike-in sequences, at least two sets of spike-in sequences, at least three sets of spike-in sequences, at least four sets of spike-in sequences or at least five sets of spike-in sequences. In a particular aspect, the invention makes use of four or five sets of spike-in sequences.

In some embodiments, a set of spike-in sequences comprises a reference sequence and a plurality of near-neighbor sequences. The reference sequences in each set of spike-in sequences differ (i.e., are independent) from each other. In some aspects, the plurality of near-neighbor sequences consists of between 2 and 10 near-neighbor sequences, between 2 and 9 near-neighbor sequences, between 2 and 8 near-neighbor sequences, between 2 and 7 near-neighbor sequences, between 2 and 6 near-neighbor sequences, between 2 and 5 near-neighbor sequences, between 2 and 4 near-neighbor sequences, or between 2 and 3 near-neighbor sequences. In some implementations, the set of spike-in sequences comprises the near-neighbor sequences at defined concentrations in relation to the reference sequences, for example, 1:10, 1:100, 1:1000, and 1:10,000. In a preferred embodiment, the collective concentration of near-neighbor sequences in a set of spike-in sequences span four orders of magnitude, for example, 1:10, 1:100, 1:1000, and 1:10,000.

The near-neighbor sequences differ from the reference sequence by at least one substitution, deletion, or insertion. In some aspects, the near-neighbor sequences are homologous sequences to the reference sequence. Accordingly, the sequence relationship between the reference sequence and its near-neighbor mimic the genetic variation conditions potentially found in a patient sample.

For example, the reference sequence functions analogously to a wild-type gene, and the near-neighbor sequences function analogously to the genetic variation found in ctDNAs. Alternatively, the reference sequence may function analogously to a mutated gene while the near-neighbor sequences function analogously to the potential variation in the mutated gene. By screening USTs in the sample using synthesis-control oligos, it will be possible to determine the dose-response characteristics of the synthesis-control oligos, which act as proxies for those of the patient-specific oligo in the assay, and thus provide a quality control check for the batch synthesis of the patient-specific oligos. Thus, the spike-in sequences are unrelated to sequences in the patient sample. Furthermore, each set of spike-in sequences are unrelated to each other. Preferably, each sequence in the USTs have different sequences.

In certain aspects, the method of validating a batch of patient-specific oligos comprises extracting DNA or RNA from a patient sample to produce a DNA or RNA sample; introducing a plurality of sets of spike-in sequences into the DNA or RNA sample to produce a spiked sample, wherein the plurality of sets of spike-in sequences consists of spike-in sequences of known concentrations; assaying the spiked sample with the synthesis-control oligos and the patient-specific oligo to produce a read out of the counts of the sets of spike-in sequences; and comparing the counts of the set of spike-in sequences with the known concentrations of the spike-in sequences. It is important that the synthesis-control oligos and the patient-specific oligo are cosynthesized in order to allow the read out from the synthesis-control oligos to validate the patient-specific oligo. Accordingly, some implementations of the method comprise cosynthesizing the synthesis-control oligo and the patient-specific oligo.

The assaying step may be performed using any primer-based method of quantifying (including both absolute and relative methods) the spiked sample using the synthesis-control oligos and the patient-specific oligo. Thus, the assay may be performed by a sequencing method or by PCR (for example, quantitative PCR or digital PCR). In a preferred embodiment, the assay is performed according to the methods described in the PCT application PCT/US17/34329, titled "Molecular Tagging Methods and Sequencing Libraries," which is hereby incorporated by reference. The counts of spike-in sequences from the assay at least enable a comparison of the concentration of the near-neighbor sequences in relation to the reference sequence. For example, a person having ordinary skill in the art would be able to calculate a ratio of the concentration of the near-neighbor sequences to the concentration reference sequence from the sequencing or PCR results.

Reading out the counts of spike-in sequences determines the limit of detection (LOD) and dynamic range of the patient-specific oligo in the assaying step by determining the ratio of the near-neighbor sequences in relation to the reference sequence from the counts with the known concentration of the near-neighbor sequences. If the assay results from the synthesis-control oligos are accurate, for example, the ratios of the near-neighbor sequences in relation to the reference sequence based on the counts is within 20%, 15%, 10%, 5%, or 1% of the ratios based on the known concentrations of spike-in sequences, and the synthesis batch of the patient-specific oligos is validated. Accordingly, one would be able to predict that the assay results from the patient-specific oligo would also be accurate. In some implementations, the plurality of set of spike-in sequences may be introduced to the sample prior to library synthesis.

In some embodiments, each set of spike-in sequences comprises a concentration such that the sum counts of a given reference plus its near-neighbors is the same as the number of genome copies in the patient sample. In some embodiments, the ratio of concentrations between a near-neighbor sequence and the reference sequence are replicated across the sets of spike-in sequences while the concentration of the reference sequence need not be the same across each set of spike-in sequences. For example, if one set of spike-in sequences comprises ratios of a near-neighbor sequence to the reference sequence of 1/10, 1/100, 1/1000, and 1:10000, at least one other set of spike-in sequence will also comprise ratios of a near-neighbor sequence to the reference sequence of 1/10, 1/100, 1/1000, and 1:10000. In implementations where the number of near-neighbor sequences differ each set of spike-in sequences, the ratio of concentration between a near-neighbor sequence and the reference in the set with the smaller number of near-neighbor sequences correspond to a ratio of concentration between a near-neighbor sequence and the reference in the set with the larger number of near-neighbor sequences. Thus, in preferred embodiments, at any ratio of concentration will contain replicates from within the same set of spike-in sequences and/or from different sets of spike-in sequences. As such, each point in the dose-response curve of the assay will have different measurements. In some embodiments, this is due to one set of spike-in sequences contributing one measurement. However, in some aspects, the amount of each near-neighbor sequence in a set of spike-in sequences is different. Nothing in the specific nucleic acid sequence of a near-neighbor sequence affects how much of the specific near-neighbor sequence should be in the set of spike-in sequences.

In some implementations, the number of sets of spike-in sequences is less than 30, for example, less than 20 sets, less than 15 sets, less than 10 sets, or preferably, less than 5 sets. In a preferred embodiment, the number of sets of spike-in sequences is four or five. In some implementations, in each set of spike-in sequences the concentration of the near-neighbor sequences as compared to the reference sequence is less than that of the reference sequence. The number of near-neighbor sequences in a set of spike-in sequences is driven by how wide a dynamic range the control oligo should measure and the precision in which to measure the dynamic range. In one embodiment, where the concentrations for all near-neighbor sequences collectively span four orders of magnitude relative to the reference sequence (for example, 1/10, 1/100, 1/1000, and 1:10000), the set of spike-in sequence comprises at least four near-neighbor sequences. Accordingly, in some embodiments, the number of near-neighbor sequences in the set of spike-in sequences is between 5 and 20, between 5 and 10, or between 10 and 20 sequences. For example, a set of spike-in sequences comprises a reference sequence and 10 near-neighbor sequences, 9 near-neighbor sequences, 8 near-neighbor sequences, 7 near-neighbor sequences, 6 near-neighbor sequences or 5 near-neighbor sequences.

In some embodiments, the present invention relates to methods wherein:
   Spike targets are single stranded oligos with a collective spread of lengths corresponding to the spread seen in a typical ctDNA sample;
   Spike targets are made in large batches and added to each patient DNA/RNA specimen prior to library synthesis;
   Spike targets each have a different sequence, unrelated to each other or to human sequences;
   Each spike target is a mixture of a reference sequence and nine near-neighbors, each with one or more substitutions;
   Each near-neighbor is spiked into the reference sequence at a defined concentration;
   The set of concentrations for all near neighbors collectively span four orders of magnitude relative to the reference sequence: for example, 1/10, 1/100, 1/1000, and 1:10,000;
   Assay oligo sets corresponding to each spike target are co-synthesized with the patient-specific assay oligos;
   A given spike target assay oligo set amplifies the reference sequence and all near-neighbors for a given set of spike targets;
   By reading out the counts of twelve reference sequences, for example, and their near-neighbors, it is possible to determine the LOD and dynamic range of each patient-specific synthesis with each sample; and/or
   Each point in the dose-response curve will have 12 different measurements, for example, one from each spike target set.

The synthesis-control oligos are oligos that are complementary to the set of spike-in sequences and, through a set of assay steps, will generate a measurable signal that reports out the nucleotide sequence of the spike-ins in-line with the patient-specific oligos. Thus, a synthesis-control oligo recognizes one reference sequence and its corresponding near-neighbor sequences. The patient-specific oligo is an oligo that is complementary to a sequence in the DNA or RNA sample. In some embodiments, the patient-specific oligo is complementary to ctDNA. In some aspects, the patient-specific oligo is complementary to an oncogene.

The disclosed methods validate patient-specific oligos for use in multiplexed patient-specific assays. In particular, the validation rules out any effect the synthesis of the oligos may have on the results of the patient-specific assays. The patient-specific oligos are usable in next generation sequencing, but they may be applied to any multiplexed DNA- or RNA-based assay where the collection of assay targets is determined by the sequence of assay oligos. Thus, the analyte may be DNA or RNA. In some aspects, the patient-specific oligos may be used for assessment of gene expression, such as the expression of a cancer-specific transcript. In some aspects, the patient-specific oligos may be used for to monitor disease development or treatment efficacy by tracking the expression of a specific transcript or detecting the presence of a particular copy of a gene. In a preferred embodiment, the patient-specific oligos are used for monitoring of cancer development and/or progression or cancer treatment efficacy using liquid biopsies, such as the detection of ctDNA.

Cell-free DNA (cfDNA) released into the bloodstream by tumors allows noninvasive identification of initial tumor-specific mutations. However, not all molecular changes in tumors involve DNA mutations; in many cases it is also the quantity of a particular gene (e.g., gene expression) that is important. In an embodiment, cfRNA released into the blood is used to monitor gene expression in cancer patients. In a particular embodiment, the PD-1/PD-L1 pathway is a promising therapeutic target and anti-PD-L1 agents have shown encouraging activity in a variety of tumor types.

In certain embodiments, cfRNA is extracted from a patient sample and subject to further analysis as described herein. To assess cell RNA quantity for a particular gene (e.g. PD-L1), plasma may be fractionated from patient collected blood. Methods of fractionating blood are known in the art and include as non-limiting examples fractionation by the Cohn method (e.g. cold ethanol fractionation), chromatography, or combinations thereof.

In yet other embodiments, the counts from oligos are read a quantitative or semi-quantitative method. Non-limiting examples of such methods include quantitative PCR (qPCR), real-time PCR, digital PCR, primer-based sequencing, It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of validating a patient-specific oligo, the method comprising:
   extracting DNA or RNA from a patient sample to produce a DNA or RNA sample;
   introducing a plurality of sets of spike-in sequences into the DNA or RNA sample to produce a spiked sample, wherein the plurality of sets of spike-in sequences comprises spike-in sequences of known concentrations;
   cosynthesizing synthesis-control oligos and the patient-specific oligo, wherein the synthesis-control oligos are complementary to the set of spike in sequences and the patient-specific oligo is complementary to a sequence in the DNA or RNA sample;
   assaying the spiked sample with the cosynthesized synthesis-control oligos and patient-specific oligo to produce a read out of the counts of the set of spike-in sequences and detect the patient-specific RNA or DNA; and
   comparing the counts from the set of spike-in sequences with the known concentrations of the spike-in sequences, wherein the limit of detection (LOD) and the dynamic range for the detection by the patient-specific oligo are validated when the counts from the set of spike-in sequences correspond to the known concentrations of the spike-in sequences.

2. A method of validating a patient-specific oligo, the method comprising:
   extracting DNA or RNA from a patient sample to produce a DNA or RNA sample;
   introducing a plurality of sets of spike-in sequences into the DNA or RNA sample to produce a spiked sample, wherein the plurality of sets of spike-in sequences comprises spike-in sequences of known concentrations;
   assaying the spiked sample with synthesis-control oligos and patient-specific oligo to produce a read out of the counts of the set of spike-in sequences and detect the patient-specific RNA or DNA, wherein the synthesis-control oligos are cosynthesized with the patient-specific oligo; and
   comparing the counts from the set of spike-in sequences with the known concentrations of the spike-in sequences, wherein the LOD and the dynamic range for the detection by the patient-specific oligo are validated when the counts from the set of spike-in sequences correspond to the known concentrations of the spike-in sequences.

3. The method of claim 2, wherein assaying the spiked sample with synthesis-control oligos comprises performing polymerase chain reaction (PCR) or sequencing with the synthesis-control oligos.

4. The method of claim 3, wherein the PCR is digital PCR or quantitative PCR.

5. The method of claim 2, wherein the plurality of set of spike sequences is introduced to the DNA or RNA sample prior to library synthesis.

6. The method of claim 2, wherein the counts of spike-in sequences act as a proxy for the dose-response characteristics of the patient-specific oligo in the assaying step.

7. The method of claim 2, wherein the plurality of sets of spike-in sequences comprises at least 4 sets of spike-in sequences.

8. The method of claim 2, wherein a set of spike-in sequences comprises:
   a reference sequence; and
   a plurality of near-neighbor sequences, wherein each near-neighbor sequence comprises at least one substitution, insertion, and/or deletion compared to the reference sequence.

9. The method of claim 8, wherein the concentration of each near-neighbor sequence is less than the concentration of the reference sequence.

10. The method of claim 8, wherein the ratios of the concentration of each near-neighbor sequence to the concentration of the reference sequence spans at least four orders of magnitude.

11. The method of claim 10, wherein the ratios of the concentration of the plurality of near-neighbor sequences to the concentration of the reference sequence comprise 1:10, 1:100, 1:1000, and 1:10,000.

12. The method of claim 8, wherein each set of spike-in sequences comprises the same number of near-neighbor sequences.

13. The method of claim 8, wherein the plurality of sets of spike-in sequences comprises the same set of ratios of the concentration of each near-neighbor sequence to the concentration of the reference sequence.

14. The method of claim 8, wherein the counts from the set of spike-in sequences corresponds to the known concentrations of the spike-in sequences when ratios of the near-neighbor sequences in relation to the reference sequence based on the counts is within 20%, 15%, 10%, 5%, or 1% of ratios of the near-neighbor sequences in relation to the reference sequence based on the known concentrations.

15. The method of claim 13, wherein the LOD and the dynamic range for the patient-specific oligo is validated when the ratios based on the counts is within 1% of the ratios based on the known concentrations.

16. The method of claim 2, wherein the patient sample is a liquid sample containing cell-free DNA (cfDNA) and/or cell-free RNA (cfRNA).

17. The method of claim 16, wherein the patient-specific oligos detect in the cfDNA and/or cfRNA a mutation and/or change in expression in a gene selected from the group consisting of PD-L1, ERCC1, EGFR, TS, AREG, EREG, VEGFR2, EML4ALK, ROS1, RET, c-Met, FGFR1, KRAS, BRAF, NRAS, Her-2, PIK3CA, KIT, GNAQ, and GNA11.

18. The method of claim 2, wherein the patient-specific oligo detects circulating tumor DNA (ctDNA).

19. The method of claim 2, wherein the patient has or is suspected of having cancer.

20. The method of claim 19, wherein the cancer is selected from the group consisting of head and neck, periampullary, colorectal, lung, melanoma, gastric, esophageal, breast, ovarian, sarcoma, renal cell, prostate, gastrointestinal stromal tumor (GIST), and pancreatic cancer.

* * * * *